(12) United States Patent
Tang et al.

(10) Patent No.: US 11,788,058 B2
(45) Date of Patent: Oct. 17, 2023

(54) PROTEIN-MODIFIED PLGA MICROSPHERE AND TISSUE-ENGINEERED NERVE CONSTRUCTED THEREWITH

(71) Applicant: NANTONG UNIVERSITY, Jiangsu (CN)

(72) Inventors: Xin Tang, Jiangsu (CN); Cheng Sun, Jiangsu (CN); Xiaosong Gu, Jiangsu (CN); Youlang Zhou, Jiangsu (CN); Chunkang Tang, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 0 days.

(21) Appl. No.: 17/596,647

(22) PCT Filed: Jun. 19, 2020

(86) PCT No.: PCT/CN2020/097111
§ 371 (c)(1),
(2) Date: Dec. 15, 2021

(87) PCT Pub. No.: WO2021/227199
PCT Pub. Date: Nov. 18, 2021

(65) Prior Publication Data
US 2022/0213437 A1 Jul. 7, 2022

(30) Foreign Application Priority Data
May 14, 2020 (CN) .......................... 202010407176.4

(51) Int. Cl.
| | | |
|---|---|---|
| *C12N 5/04* | (2006.01) | |
| *C12N 5/0793* | (2010.01) | |
| *A61L 27/26* | (2006.01) | |
| *B82Y 5/00* | (2011.01) | |
| *C07K 14/78* | (2006.01) | |

(52) U.S. Cl.
CPC ............ *C12N 5/0619* (2013.01); *A61L 27/26* (2013.01); *B82Y 5/00* (2013.01); *C07K 14/78* (2013.01); *A61L 2400/12* (2013.01); *A61L 2430/32* (2013.01); *C12N 2533/00* (2013.01)

(58) Field of Classification Search
CPC ... C12N 5/0619; C12N 2533/00; A61L 27/26; A61L 2400/12; A61L 2430/32; A61L 2300/30; A61L 2300/412; A61L 2300/622; A61L 27/227; A61L 27/18; A61L 27/34; A61L 27/54; A61L 27/24; A61L 27/50; A61L 2300/414; A61L 2300/602; B82Y 5/00; C07K 14/78; A61K 36/16; A61K 38/00; A61K 9/1647; A61K 9/1658; A61K 36/77; A61K 36/8988; A61P 25/00
See application file for complete search history.

(56) References Cited

U.S. PATENT DOCUMENTS

| | | |
|---|---|---|
| 2007/0178135 A1 | 8/2007 | Zhong |
| 2011/0236974 A1 | 9/2011 | Ogle et al. |
| 2019/0105261 A1* | 4/2019 | Waugh ................. A61K 31/167 |

FOREIGN PATENT DOCUMENTS

| | | |
|---|---|---|
| CN | 1285725 C | 11/2006 |
| CN | 103364568 A | 10/2013 |
| CN | 103894328 A | 7/2014 |
| CN | 104399131 A | 3/2015 |
| CN | 106215245 A | 12/2016 |
| CN | 106619537 A | 5/2017 |
| CN | 107224571 A | 10/2017 |
| CN | 107427533 A | 12/2017 |
| CN | 108525017 A | 9/2018 |

OTHER PUBLICATIONS

Chang et al., "Polymeric nanofibrous nerve conduits coupled with laminin for peripheral nerve regeneration", Biomed Mater. 15(3), pp. 2-26, Mar. 2020.*
Zhao et al., "Polylactic-co-glycolic acid microspheres containing three neurotrophic factors promote sciatic nerve repair after injury", Neural Regeneration Research, 10(9), Sep. 2015.*
Huang, Y.; Huang, C.; Huang, Y.; Chen, K. Surface modification and characterization of chitosan or PLGA membrane with laminin by chemical and oxygen plasma treatment for neural regeneration. J. Biomed. Mat. Res. Part A, pp. 842-851. (Year: 2006).*
Zhang, Junjiang; Synthesis and characterization of silk fibroin; Chinese Master's Theses Full-text Database Engineering Science and Technology, Feb. 15, 2019, ISSN 1674-0246, B016-918.
Zhu, Jiakai et al.; MORDEN peripheral neurological surgery; Shanghai Scientific and Technical Publishers, ISBN 978-7-5323-8809-7 Oct. 31, 2007, pp. 321.
Zhu, Qingtang et al.; Biofabrication and clinical evaluation of peripheral nerve repair materials; Zhong Shan University Press, ISBN 978-7-306-06388-5, Sep. 30, 2018, pp. 311-313.
Newman, Kimberley D et al.; Poly(D, L lactic-co-glycolic acid) microspheres biodegradable microcarriers for pluripotent stem cells; Biomaterials, vol. 25, Issue 26, pp. 5763-5771, Nov. 30, 2004.
Liu, Yaoshan et al.; Silk Fibroin-modified Ploylactic Acid-glycolic Acid Copolymer Porous Microspheres as Gingival Mesenchymal Stem Cells Delivery Carrier; Chemical Journal of Chinese Universities; vol. 4, No. 11, pp. 2419-2426, Nov. 30, 2019.
Liu, Yinong et al.; Encapsulation of Proteins in PLGA Microsphere gelatin Composite Scaffold; Progress in Modern Biomedicine, vol. 13, No. 33, pp. 6463-6465, Nov. 30, 2013.
Su, Huanpeng et al.; Optimized Preparation of Brucea Javanica Oil-loaded Polylactic-co-glycolic Acid Microsphere by Central Composite Design-response Surface Methodology; Guang Dong chemical, vol. 43, No. 317, pp. 22-24, Dec. 31, 2016.

(Continued)

*Primary Examiner* — Jessica Worsham
(74) *Attorney, Agent, or Firm* — NKL Law; Allen Xue

(57) ABSTRACT

A protein-modified PLGA microsphere can be used to construct tissue-engineered nerve. The microspheres are loaded with active substances for treating peripheral nerve injury and are bound to tissue-engineered nerves. It has been shown that the prepared tissue-engineered nerve effectively promotes nerve regeneration after peripheral nerve injury.

7 Claims, 8 Drawing Sheets

(56) References Cited

OTHER PUBLICATIONS

Zhang, Tianzhu et al.; The controllable preparation of porous PLGA microspheres by the oil/water emulsion method and its application in 3D culture of ovarian cancer sells; < Colloids and Surfaces A:Physicochemical and Engineering Aspects>, Apr. 2, 2014; vol. 452, pp. 115-124.

* cited by examiner

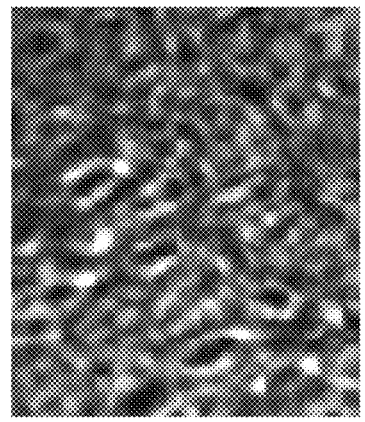
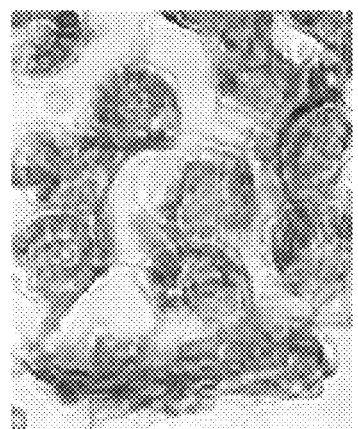
FIG. 7A
| (μm) | Control | 2mg/mL | 10mg/mL | 50mg/mL | 250mg/mL |
|---|---|---|---|---|---|
| Axon diameter | 2.63±0.23 | 2.74±0.33 | 5.35±0.20** | 5.95±0.31** | 2.72±0.35 |
| Myelin thickness | 1.59±0.36 | 1.63±0.21 | 2.35±0.33 | 3.76±0.27* | 1.65±0.21 |
FIG. 7B

PROTEIN-MODIFIED PLGA MICROSPHERE AND TISSUE-ENGINEERED NERVE CONSTRUCTED THEREWITH

BACKGROUND

Technical Field

The present invention relates to the technical field of biomedicine, and specifically to a protein-modified PLGA microsphere, and a tissue-engineered nerve constructed therewith that is useful in repairing peripheral nerve defects.

Related Art

Peripheral nerve injury is a common disease in clinic, which usually leads to paralysis, palsy and even loss of autonomous control of corresponding body parts, which seriously affects the quality of life of patients. At present, the surgical repair effect of simply suturing the severed nerve is not satisfactory, and autologous nerve transplantation, which is the gold standard for repairing peripheral nerve defects, is limited in clinical application due to the inadequate source of autologous nerve donors and secondary damage caused by the transplantation. Therefore, constructing suitable tissue-engineered nerves to replace autologous nerves to repair peripheral nerve defects has broad application prospects.

Tissue-engineered nerves are generally composed of nerve conduit scaffolds, combined with multiple growth factors or seed cells and other factors.

However, seed cells often suffer many problems such as inadequate source or immunogenicity of allogeneic cells, and thus have limitation in clinical application. Adding growth factors to a scaffold material requires consideration of maintaining stability and efficiency according to their physical and chemical properties.

Therefore, the development of new biologically active materials capable of repairing nerve damage and combining them with tissue-engineered nerves have a wider clinical application value.

SUMMARY

A preliminary study of the present invention (Chinese Patent Application No. 2020103158417) discloses a fat-soluble extract of *Brucea javanica* L. Merr. It is found through research that the fat-soluble extract of *Brucea javanica* L. Merr promotes the growth of peripheral DRG neurons and neurites, and promotes the division and proliferation of the glial cells, that is, Schwann cells, of the peripheral nervous system, thus promoting peripheral nerve regeneration. In the present invention, a protein-modified PLGA microsphere is designed on this basis, and the fat-soluble extract of *Brucea javanica* L. Merr is used as an active substance to construct tissue-engineered nerves. In the present invention, the fat-soluble extract of *Brucea javanica* L. Merr is combined with laminin-modified PLGA microspheres to prepare laminin-PLGA-fat-soluble extract of *Brucea javanica* L. Merr microspheres with sustained action of release, which can significantly promote the axon growth of DRG neurons in vitro. Further, the sustained-release microspheres containing the fat-soluble extract of *Brucea javanica L. Merr* are bound to the silk fibroin fibers in the silk fibroin nerve conduit to construct a tissue-engineered nerve containing laminin-PLGA-fat-soluble extract of *Brucea javanica L. Merr* microspheres. In-vivo experiments prove that the tissue-engineered nerve can effectively promote the myelination of the regenerated nerve after peripheral nerve injury, providing a new option for clinical treatment of peripheral nerve injury.

The following specific technical solution is adopted in the present invention.

A protein-modified PLGA microsphere is provided, where PLGA is cross-linked with one or more of collagen, fibronectin, silk fibroin, and laminin through a cross-linking agent. The crosslinking agent is a chemical crosslinking agent or a biological crosslinking agent, preferably a biological crosslinking agent, such as genipin, carbodiimide/N-hydroxysuccinimide (EDC/NHS), and sodium alginate, preferably genipin.

Preferably, the weight ratio of the protein to PLGA is 1:1-10, and more preferably, 1:3.

Preferably, the weight ratio of the fat-soluble extract of *Brucea javanica* L. Merr to PLGA is 1-10:1, and more preferably, 3-5:1.

A preferred embodiment of the present invention is laminin-modified PLGA sustained-release microspheres.

The microspheres of the present invention can be loaded with active substances for treating peripheral nerve injury. The active substance is one or more selected from cells, polysaccharides, polypeptides, proteins, nucleic acids, compounds or natural extracts, for example, one or more of neurotrophic factors, cell growth factors, extracellular matrix, Ginkgo biloba extract, *Gastrodia* extract, and fat-soluble extract of *Brucea javanica* L. Merr.

In a specific embodiment of the present invention, the fat-soluble extract of *Brucea javanica L. Merr* is used as the active substance. Preferably, the fat-soluble extract of *Brucea javanica L. Merr* is obtained by extraction with a mixed solution of absolute ethanol and ethyl acetate, where the percentage by volume of absolute ethanol is 45%-85%. More preferably, the percentage by volume of absolute ethanol in the mixed solution is 75%. Further, ultrasonic extraction can be used. Preferably, the ultrasonic frequency is 20 kHz, the power is 750 W, the time is 60 min, and the material-to-liquid ratio is 1:5 g/mL.

The microspheres of the present invention have smooth surface and uniform particle size (bar=5 μm); and the diameter of the microspheres is mostly concentrated at 2.5 μm.

Another object of the present invention is to provide use of the protein-modified PLGA microspheres in preparing medicines for treating peripheral nerve defects or tissue-engineered nerves. In the present invention, PLGA is modified with an active protein, which can not only improve the biocompatibility of PLGA sustained-release microspheres and the biological activity of the material and allow the prepared microspheres to have good sustained releasability, and also promote the adhesion and growth of nerve cells.

The present invention investigates the effect of laminin modified PLGA-fat-soluble extract of *Brucea javanica* L. Merr sustained-release microspheres prepared with laminin at different concentrations on the axon growth of DRG neurons cultured in vitro. The results show that the sustained-release microspheres prepared with 1-3 mg/ml laminin can promote the axon growth of DRG neurons, and the sustained-release microspheres prepared with 1 mg/ml laminin have the most preferred effect in promoting the growth of DRG neurons, which is significantly better than the cases with a higher concentration of 9 mg/ml, and a lower concentration of 0.33 mg/ml and 0.11 mg/ml laminin.

Another object of the present invention is to provide a tissue-engineered nerve loaded with protein-modified PLGA microspheres. Protein-modified PLGA microspheres loaded with active substances for treating peripheral nerve injury are loaded on the inner/outer surface or inside of the tissue-engineered nerve by one or more of adsorption, coating, mixing, embedding, crosslinking with a crosslinking agent, three-dimensional printing and electrostatic spinning.

The tissue-engineered nerve can be prepared with materials commonly used in the prior art, such as silk fibroin, chitosan, polyglycolic acid, polycaprolactone, collagen, polylactic acid and gelatin, in shapes commonly used in the prior art, such as conduits, stents, surgical sutures, etc. Furthermore, the tissue-engineered nerve has pores or simulated nerve fibers inside.

Preferably, the tissue-engineered nerve of the present invention is a silk fibroin nerve conduit, and further, there are fibers in the conduit.

According to a preferred embodiment of the present invention, laminin modified PLGA-fat-soluble extract of Brucea javanica L. Merr sustained-release microspheres are immobilized on silk fibroin fibers by a biological crosslinking agent genipin to obtain silk fibroin fibers with laminin modified PLGA-fat-soluble extract of Brucea javanica L. Merr sustained-release microspheres. The silk fibroin fiber with laminin modified PLGA sustained-release microspheres was assembled into silk fibroin nerve conduit. The silk fibroin nerve conduit has a length of 10 mm, an outer diameter of about 2.2 mm and an inner diameter of about 1.5 mm. Generally, ten silk fibroin fibers containing the fat-soluble extract of Brucea javanica L. Merr sustained-release microspheres were loaded into each silk fibroin nerve conduit in parallel, to construct the tissue-engineered nerve containing the fat-soluble extract of Brucea javanica L. Merr sustained-release microspheres.

According to the present invention, the constructed tissue-engineered nerve containing the fat-soluble extract of Brucea javanica L. Merr sustained-release microspheres is used in repairing a rat sciatic nerve defect model, and myelination of regenerated nerve is observed 12 weeks after operation. The results show that the thickness of myelin sheath in the experimental group with treated microspheres prepared by loading 10 mL of 10 mg/mL fat-soluble extract of Brucea javanica L. Merr on the microspheres is better than that in the negative control group. Compared with the negative control group treated with laminin modified PLGA sustained-release microsphere without the fat-soluble extract of Brucea javanica L. Merr, there are significant differences in axon diameter and myelin sheath thickness in the experimental group treated with microspheres prepared by loading 10 mL of 50 mg/mL fat-soluble extract of Brucea javanica L. Merr on the microspheres.

The present invention has the following advantages.

1. In the present invention, PLGA with a larger molecular weight of 50-75 kDa is used to prepare microspheres. A larger molecular weight can effect a longer release period, which is suitable for the needs in the initial critical stage of peripheral nerve regeneration. By modifying PLGA with natural macromolecular proteins or extracellular matrix proteins, the repair of nerve injuries is promoted by taking advantage of the properties of these proteins. The prepared microspheres also have a sustained action of release, particularly laminin-modified PLGA microspheres have a long sustained-release period and the best sustained-release effect.

2. A preliminary study of the present invention finds that the fat-soluble extract of Brucea javanica L. Merr prepared by extraction with a mixed solution of absolute ethanol and ethyl acetate at a specific ratio combined with ultrasound can significantly promote the axon growth of peripheral DRG neurons and promote the division and proliferation of peripheral glial cells, that is, Schwann cells, suggesting that the fat-soluble extract of Brucea javanica L. Merr can promote peripheral nerve regeneration. In the present invention, the fat-soluble extract of Brucea javanica L. Merr is combined with laminin-modified PLGA sustained-release microspheres to prepare laminin-PLGA-fat-soluble extract of Brucea javanica L. Merr sustained-release microspheres. The microspheres have the advantages of good biocompatibility, easy modification, uniform particle size, and regular morphology, and can achieve an effective sustained action of release with a long release period. Further, the laminin-PLGA-fat-soluble extract of Brucea javanica L. Merr sustained-release microspheres are bound to the silk fibroin fibers in the silk fibroin nerve conduit to successfully construct a tissue-engineered nerve containing the fat-soluble extract of Brucea javanica L. Merr sustained-release microspheres. In-vivo experiments find that the tissue-engineered nerve can effectively promote the myelination of the regenerated nerve after peripheral nerve injury.

BRIEF DESCRIPTION OF THE DRAWINGS

(FIG. 2A shows the immunohistochemical staining of axon growth of DRG neurons promoted by various dosages of the fat-soluble extract of Brucea javanica L. Merr; and FIG. 2B is a histogram showing the statistical result of growing axon length of DRG neuron promoted by various dosages of the fat-soluble extract of Brucea javanica L. Merr.

FIGS. 3A and 3B show EdU staining to detect the effect of the fat-soluble extract of Brucea javanica L. Merr on the proliferation of Schwann cells. (FIG. 3A shows the EdU staining of Schwann cell proliferation promoted by various dosages of the fat-soluble extract of Brucea javanica L. Merr; and FIG. 3B is a histogram showing the statistical result of Schwann cell proliferation promoted by various dosages of the fat-soluble extract of Brucea javanica L. Merr.

FIG. 6B is a histogram of the diameter of the laminin-PLGA-fat-soluble extract of Brucea javanica L. Merr sustained-release microspheres; and FIG. 6C is a histogram of fluorescence immunocytochemical staining).

FIGS. 7A and 7B show trichrome staining of the nerve to observe the myelination of regenerated nerve after repair with a tissue-engineered nerve (FIG. 7A is a representative image of trichrome staining of the nerve; FIG. 7B shows the statistical result of trichrome staining of the nerve).

DETAILED DESCRIPTION

Figure 1:
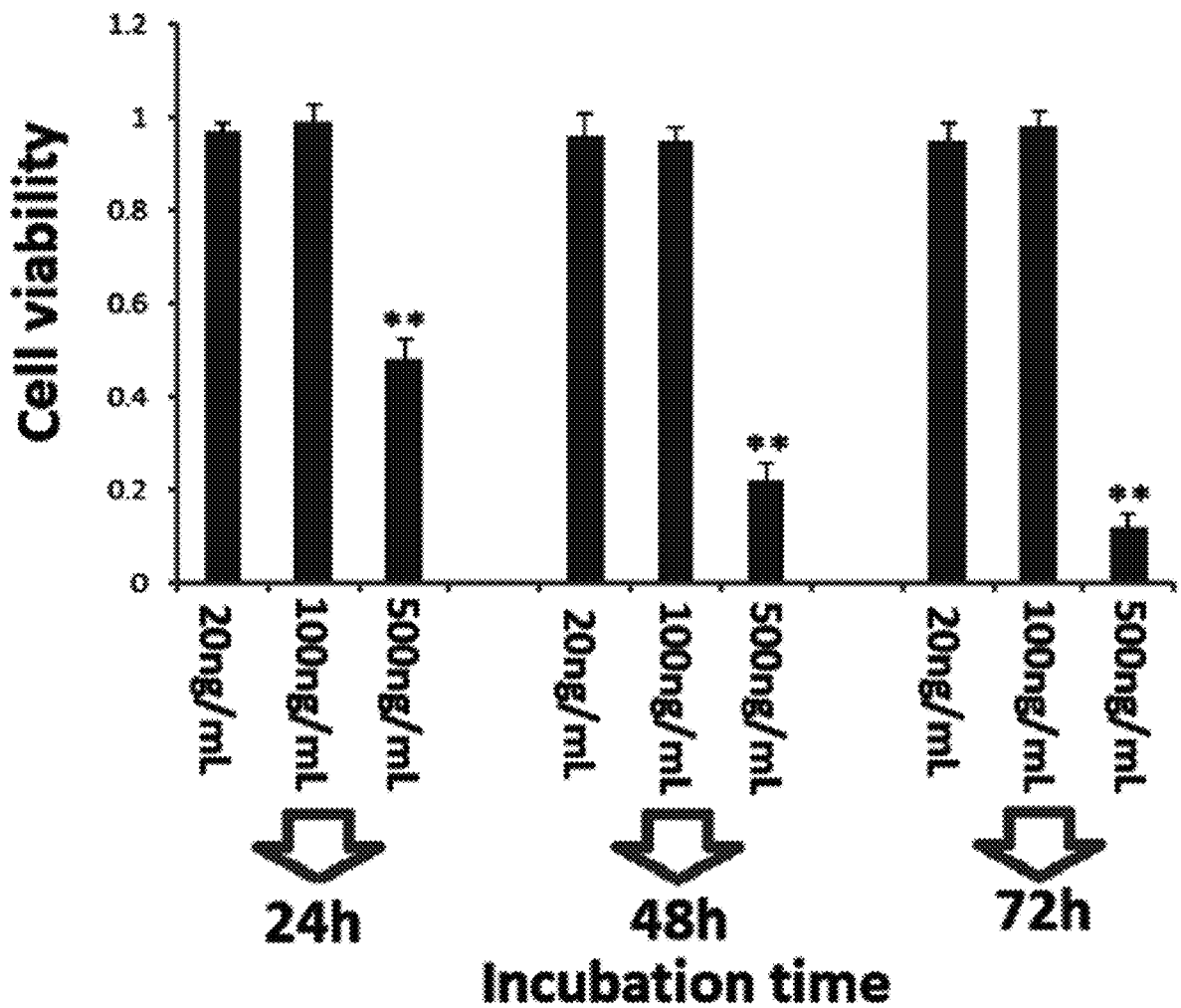
FIG. 1 shows the cytotoxicity of the fat-soluble extract of Brucea javanica L. Merr detected by CCK8.

Specific steps of the present invention are described below based on embodiments, but the present invention is not limited to the embodiments.

The terms used in the present invention, unless otherwise stated, generally have the meaning commonly understood by a person of ordinary skill in the art.

The present invention is further described below in detail with reference to specific examples and data. It should be understood that the embodiments are only for describing the present invention by using examples, but do not limit the scope of the present invention in any manner.

In the following embodiments, various processes and methods that are not described in detail are common conventional methods in the art.

Example 1. Preparation of the Fat-Soluble Extract of Brucea javanica L. Merr The fat-soluble extract of Brucea javanica L. Merr was prepared according to the method disclosed in CN2020103158417.

Brucea javanica L. Merr of family Simaroubaceae, purchased from the traditional Chinese medicine (TCM) pharmacy of Nantong Hospital of Traditional Chinese Medicine, was washed with deionized water, dried in an oven at 60-65° C. for 2 days and then ground into powder (300 g). 50 g of dry Brucea javanica L. Merr powder was accurately weighed, fed to an extraction vessel, and soaked in a mixed solution of absolute ethanol and ethyl acetate of various concentrations at room temperature (22° C.) for 48 hrs. Groups: 95% absolute ethanol+5% ethyl acetate; 85% absolute ethanol+15% ethyl acetate; 75% absolute ethanol+25% ethyl acetate; 65% absolute ethanol+35% ethyl acetate; 55% absolute ethanol+45% ethyl acetate; 45% absolutee ethanol+55% ethyl acetate; 35% absolute ethanol+65% ethyl acetate; 25% absolute ethanol+75% ethyl acetate; 15% absolute ethanol+85% ethyl acetate; 5% absolute ethanol+95% ethyl acetate. The soak solutions of various concentrations were further ultrasonically extracted at an ultrasonic frequency of 20 kHz, a power of 750 W, and a material-to-liquid ratio of 1:5 g/mL for a time of 60 min. The resulting solutions were filtered through Whatman No. 1 filter paper, and then evaporated in a rotary evaporator (Buchi rotavapor R-124) under reduced pressure and concentrated at 40° C. After most of the solvent was removed, the extract fractions A (about 18-23 g) of Brucea javanica L. Merr seeds extracted with different extraction solutions were obtained, and stored in a refrigerator at −20° C. for later use.

Example 2. Extraction Effect of Various Concentrations of Mixed Solutions of Absolute Ethanol and Ethyl Acetate In order to detect the effect of the fat-soluble extract of Brucea javanica L. Merr extracted with various concentrations of absolute ethanol and ethyl acetate on the growth of nerve cells, the nerve cell line PC12 cells were used as the observation model in the experiment.

PC12 cells were cultured in DMEM complete medium (containing 10% horse serum, 5% fetal bovine serum, 100 U/ml penicillin, and 100 μg/ml streptomycin) in a culture dish which was placed in an incubator at 5% $CO_2$ and 37° C. The medium was refreshed every two days and the cells were subcultured when grown to 80% confluence. In the experiment, PC12 cells in logarithmic growth phase were inoculated at $5\times10^4$/ml into a 24-well culture plate in 400 μl per well. After 24 hrs, the medium was replaced by a DMEM medium containing 1% horse serum and 1% fetal bovine serum. In the experiment, a negative control group with DMEM medium including 1% horse serum and 1% fetal bovine serum, and experimental groups treated with 100 ng/mL extract obtained by extraction with a mixed solution of different concentrations of absolute ethanol and ethyl acetate, were respectively set. After 3-d culture with the extract, the morphological changes of PC12 cells were observed under an inverted microscope. 50 cells were randomly selected from each group, and the positive cell rate, axon length and number of axons were measured.

The results in Table 1 show that after the PC12 cells are treated 3 days with the fat-soluble extracts of Brucea javanica L. Merr prepared by using mixed solutions of absolute ethanol and ethyl acetate at different concentrations, the extract prepared by using a combination of 75% absolute ethanol+25% ethyl acetate has the most significant effect of promoting the growth and differentiation of nerve cells (**$p<0.01$*$p<0.05$) with respect to the positive cell rate, axon length and number of axons, compared with the negative control group with DMEM medium containing 1% horse serum and 1% fetal bovine serum. It is suggested that 75% absolute ethanol+25% ethyl acetate is the most preferred concentration combination for extraction.

TABLE 1

Effects of extracts prepared by using mixed solutions of absolute ethanol and ethyl acetate at different concentrations on PC12 cells

| Experiment group | Positive cell rate/% | Axon length/μm | Number of axons |
| --- | --- | --- | --- |
| Control | 0.08 ± 0.05 | 7.50 ± 0.82 | 0.61 ± 0.30 |
| 95% absolute ethanol + 5% ethyl acetate | 0.09 ± 0.02 | 7.81 ± 0.98 | 0.82 ± 0.11 |
| 85% absolute ethanol + 15% ethyl acetate | 0.22 ± 0.08 | 9.22 ± 1.42 | 1.21 ± 0.12* |
| 75% absolute ethanol + 25% ethyl acetate | 0.85 ± 0.09** | 22.48 ± 2.05** | 2.82 ± 0.31** |
| 65% absolute ethanol + 35% ethyl acetate | 0.42 ± 0.11* | 12.34 ± 1.64* | 0.93 ± 0.28 |
| 55% absolute ethanol + 45% ethyl acetate | 0.23 ± 0.13 | 10.52 ± 1.67 | 0.91 ± 0.25 |
| 45% absolute ethanol + 55% ethyl acetate | 0.21 ± 0.12 | 8.98 ± 1.32 | 0.89 ± 0.32 |
| 35% absolute ethanol + 65% ethyl acetate | 0.17 ± 0.06 | 8.21 ± 1.42 | 0.81 ± 0.15 |
| 25% absolute ethanol + 75% ethyl acetate | 0.13 ± 0.07 | 7.98 ± 0.95 | 0.79 ± 0.23 |
| 15% absolute ethanol + 85% ethyl acetate | 0.11 ± 0.07 | 7.62 ± 1.12 | 0.71 ± 0.23 |
| 5% absolute ethanol + 95% ethyl acetate | 0.06 ± 0.05 | 7.55 ± 0.92 | 0.51 ± 0.38 |

Example 3. Cytotoxicity Test of the Fat-Soluble Extract of *Brucea javanica* L. Merr The fat-soluble extract of *Brucea javanica* L. Merr prepared in Example 1 was lyophilized overnight (EYELA FDU-1200, Tokyo), and the prepared powder was fed to a 15 ml centrifuge tube and stored at 4° C. A 10 µg/mL solution was formulated in sterile deionized water, and centrifuged at 8000 g for 10 min. Then the solution was diluted to each concentration required in the experiment, and then sterilized by filtering through a 0.2 mm nylon syringe filter (Millipore, USA) for cytotoxicity test in culturing PC12 cell line. The CCK8 kit was purchased from Dojindo Laboratories, Japan.

PC12 cells in the logarithmic growth phase were digested, counted and then re-suspended. The cells were adjusted to have a density of $5 \times 10^5$/mL, and inoculated in a 96-well plate in 100 µL per well. After the cells were attached to the wall, the medium was discarded, and the cells were wash with 0.01 M PBS for 5 min (×2). The negative control group was a group treated with a DMEM medium containing 1% horse serum and 1% fetal bovine serum. The fat-soluble extract of *Brucea javanica* L. Merr in different concentrations of 20 ng/mL, 100 ng/mL and 500 ng/mL was added to each experimental group. and the cells were cultured for 24 hrs, 48 hrs and 72 hrs respectively. The medium was gently discarded, 10% CCK8 in medium was added in an amount of 100 µLCCK8 per well (that is, 10 µl of CCK8 per 100 µl of medium was added), and the cells were continuously cultured for 2 hrs. The absorbency (OD value) of each group was measured on a microplate reader at 450 nm. The relative survival rate (%) was calculated according to the following formula: Relative survival rate (%)=[(OD of experimental group−OD of blank group)/(OD of control group—OD of blank group)]×100%. Each group had 8 replicates.

FIG. 1 shows the cytotoxicity test result of the fat-soluble extract of *Brucea javanica* L. Merr detected by CCK8. The test results by CCK8 show that the fat-soluble extract of *Brucea javanica L. Merr* at a low concentration of 20 ng/mL and a medium concentration of 100 ng/mL has no obvious cytotoxicity within 72 hours of experimental observation, while the fat-soluble extract of *Brucea javanica* L. Merr at a high concentration of 500 ng/mL shows a significant cytotoxicity from the experimental observation timepoint of 24 hrs compared with the culture with the low concentration 20 ng/mL and the medium concentration 100 ng/mL, suggesting that high concentration of the fat-soluble extract of *Brucea javanica* L. Merr is cytotoxic to nerve cells. The vertical coordinate shows the cell viability of PC12 cells cultured with each concentration of the fat-soluble extract of *Brucea javanica* L. Merr in the experimental group, which is expressed in viability percentage of PC12 cells cultured in the negative control group with DMEM medium containing 1% horse serum and 1% fetal bovine serum. ** $p<0.01$.

Example 4. Effect of the Fat-Soluble Extract of *Brucea javanica* L. Merr on the Axon Growth of DRG Neurons SD rats at 15 days of pregnancy were narcotized by intraperitoneally injecting with 10% chloral hydrate (0.2 mL/100 g), shaved, and disinfected by spraying 75% alcohol. The embryo was taken out of the womb and placed in a sterile dish filled with pre-cooled D-Hank's medium. Then the dish was placed on ice, the dorsal root ganglia was removed under a dissecting microscope, and the fascia on the surface of the ganglia was peeled off as much as possible. The dorsal root ganglia were cut to have a size of about 0.5 mm$^3$ by ophthalmic scissors, digested with 0.25% trypsin at 37° C. for 15 min, and then terminated with serum. After centrifugation, the single-cell suspension was inoculated at a cell density of $5 \times 10^5$/mL in a 24-well plate fitted with glass slides and pre-coated with PDL. The system was placed in an incubator at 37° C., and 5% $CO_2$, and the cells were incubated with 10% FBS and 90% DMEM. After the cells were attached, the cells in the negative control group were cultured with 97% Neurobasal+2% B27+1% GluMAX medium. The fat-soluble extract of *Brucea javanica* L. Merr in different concentrations of 20 ng/mL, 100 ng/mL and 500 ng/mL was respectively added to each experimental group, and the DRG neurons were continuously cultured for 72 hrs.

After the DRG neurons were cultured for 72 hours according to the above method, the medium was aspirated, and the cells were washed once with 0.01 M PBS. 500 µL of 4% paraformaldehyde was added, and the cells were fixed at room temperature for 30 min. The fixative was removed, and the cells were washed with 0.01 M PBS for 10 min (×3) at room temperature. The plate was blocked with 0.01 M PBS containing 10% goat serum and 0.3% Triton X-100 at 37° C. for 60 min, and then the blocking buffer was removed.

Fluorescence immunocytochemical analysis: The primary antibody (goat anti-GAP-43 polyclonal antibody, 1:200) was dripped, stood overnight at 4° C., and washed with 0.01 M PBS for 10 min (×3). The secondary antibody (FITC donkey anti-goat IgG, 1:200) was dripped, and the cell nucleus was labeled with Hoechst33342 (5 µg/ml), stood at room temperature for 1 hr in the dark. The cells were then washed with 0.01 M PBS for 10 min (×3). A blank control group without primary antibody was set in the experiment. For the blank control group, the steps were the same as above except that in the step (3), the goat anti-GAP-43 polyclonal antibody was replaced by 0.01 M PBS. Under a laser confocal microscope (FITC excitation wavelength: 488 nm, observation wavelength: 500-535 nm; Hoechst33342 argon-ion Ar excitation wavelength: 353-364 nm, observation wavelength: 460-480 nm), the results of fluorescence immunocytochemical detection were observed.

Figure 2A:
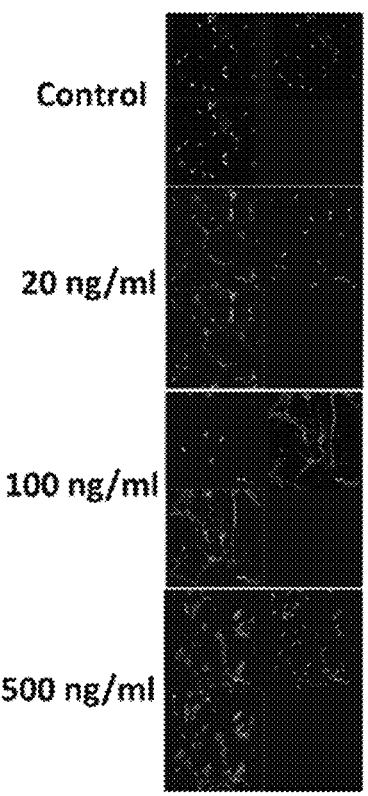
FIGS. 2A and 2B show the effect of the fat-soluble extract of Brucea javanica L. Merr on the axon growth of DRG neurons detected by immunohistochemistry.
Figure 2B:
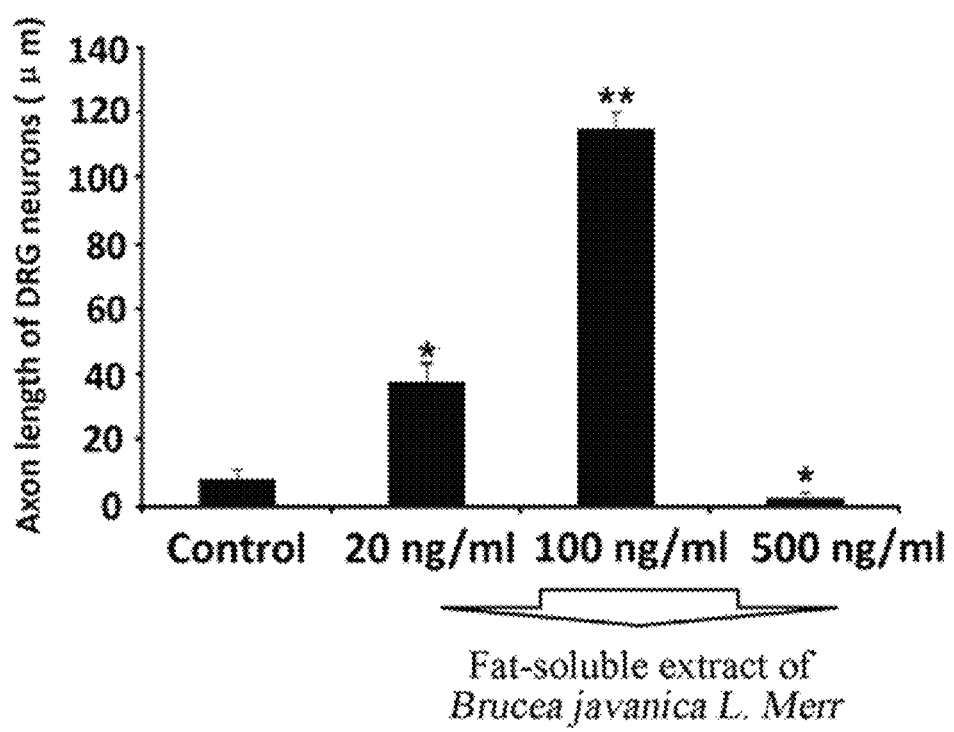

FIGS. 2A and 2B show the effect of the fat-soluble extract of *Brucea javanica* L. Merr on the axon growth of DRG neurons detected by immunohistochemistry. (FIG. 2A shows the immunohistochemical staining of axon growth of DRG neurons promoted by various dosages of the fat-soluble extract of *Brucea javanica* L. Merr; and FIG. 2B is a histogram showing the statistical result of growing axon length of DRG neuron promoted by various dosages of the fat-soluble extract of *Brucea javanica* L. Merr. The results in FIGS. 2A and 2B show that compared with the negative control group treated with 97% Neurobasal+2% B27+1% GluMAX medium and DRG neurons cultured with a low concentration of the extract, when the concentration of the fat-soluble extract of *Brucea javanica* L. Merr. is 100 ng/ml, the number and length of axons marked with GAP-43 of DRG neurons increase significantly. The fat-soluble extract of *Brucea javanica* L. Merr at a high concentration of 500 ng/ml has no promotion on DRG neurons, and the growth promotion effect is even lower than the fat-soluble extract of *Brucea javanica* L. Merr. at a low concentration of 20 ng/ml. It is suggested that the fat-soluble extract of *Brucea javanica* L. Merr at an appropriate medium concentration of 100 ng/ml can significantly promote the axon growth of DRG neurons (** $p<0.01$ * $p<0.05$).

Example 5. Effect of the Fat-Soluble Extract of *Brucea javanica* L. Merr on the Proliferation of Schwann Cells 1. Culture and Purification of Schwann Cells 1-2 day-old newborn SD rats were freeze narcotized and disinfect with 75% alcohol. The sciatic nerve was exposed and isolated through the posterolateral femoral muscle space, and soaked in pre-cooled HBSS solution. The epineurium was carefully removed under a dissecting microscope. The sciatic nerve was cut in 200 μl mg/ml collagenase, digested for 30 min at 37° C. The collagenase was removed, and 0.125% trypsin was added for digestion at 37° C. for 12 min. The digestion was terminated, the system was centrifuged and the supernatant was discarded. The cells were inoculated at a cell density of $1 \times 10^6$ to a plate pre-coated with PDL, and incubated in an incubator at 37° C. and 5% $CO_2$. The medium was replaced by a medium containing cytarabine (1:1000) within 24 hrs. The cells were purified after growth to 80% confluence. The cells were digested into a cell suspension with 0.125% trypsin, and then terminated with serum. Anti-thy1.1 (1:1000) was added and the cells were incubated on ice for 2 hrs. After centrifugation, the supernatant was discarded. A mixed solution containing 250 μl of rabbit complement and 750 μl of DMEM medium (1:3) was added and the cells were incubated at 37° C. for 1 hr. The cells were re-suspended and then inoculated at a cell density of $3 \times 10^5$ to a plate pre-coated with PDL. Moreover, 2 μM forsokolin and 10 ng/ml HRG were added to the dish, and the medium was refreshed every 3 days.

2. Detection of Cell Proliferation by EdU

Schwann cells in the 96-well plate were treated for 24 hrs with the fat-soluble extract of *Brucea javanica* L. Merr at a different concentration of 20 ng/mL, 100 ng/mL, and 500 ng/mL. The cells were detected with the Cell-Light™ EdU DNA cell proliferation kit available from Guangzhou Ribo-Bio Company following the experimental operation in the manual. The EdU solution (reagent A) was diluted with the cell culture medium at a ratio of 1:1000 to prepare an appropriate amount of 50 μEdU medium. 100 μL of 50 μM EdU medium was added to each well and the cells were incubated at 37° C. for 2 hrs. The medium was discarded, and the cells were washed with PBS for 5 min (×3). 50 μL of 4% paraformaldehyde was added to each well to fix the cells for 15 min at room temperature, and then the fixative was discarded. 50 μL of 2 mg/mL glycine was added to each well and the cells were incubated for 5 min. The glycine solution was discarded, and the cells were washed with PBS for 5 min (×3). 100 μL of a penetrant (0.5% TritonX-100 in PBS) was added to each well and the cells were incubated for 10 min. The cells were washed with PBS for 5 min (×3). 100 μL of 1× Apollo® staining reaction solution was added to each well, and the cells were incubated for 30 min in the dark at room temperature. The staining reaction solution was discarded. 100 μL of a penetrant (0.5% TritonX-100 in PBS) was added and the cells were washed on a decolorizing shaker for 10 min (×3). The penetrant was discarded. 100 μL of methanol was added to each well and the cells were washed for 5 min (×3). 5 μg/mL Hoechst 33342 reaction solution was added and the cells were incubated for 30 min. The staining reaction solution was discarded and the cells were washed with PBS for 10 min (×3). 5 low-magnification fields of each sample at 20× magnification were randomly selected, and the images were collected Leica DC 300 and analyzed by Leica QWin analysis software.

Figures 3A, 3B:
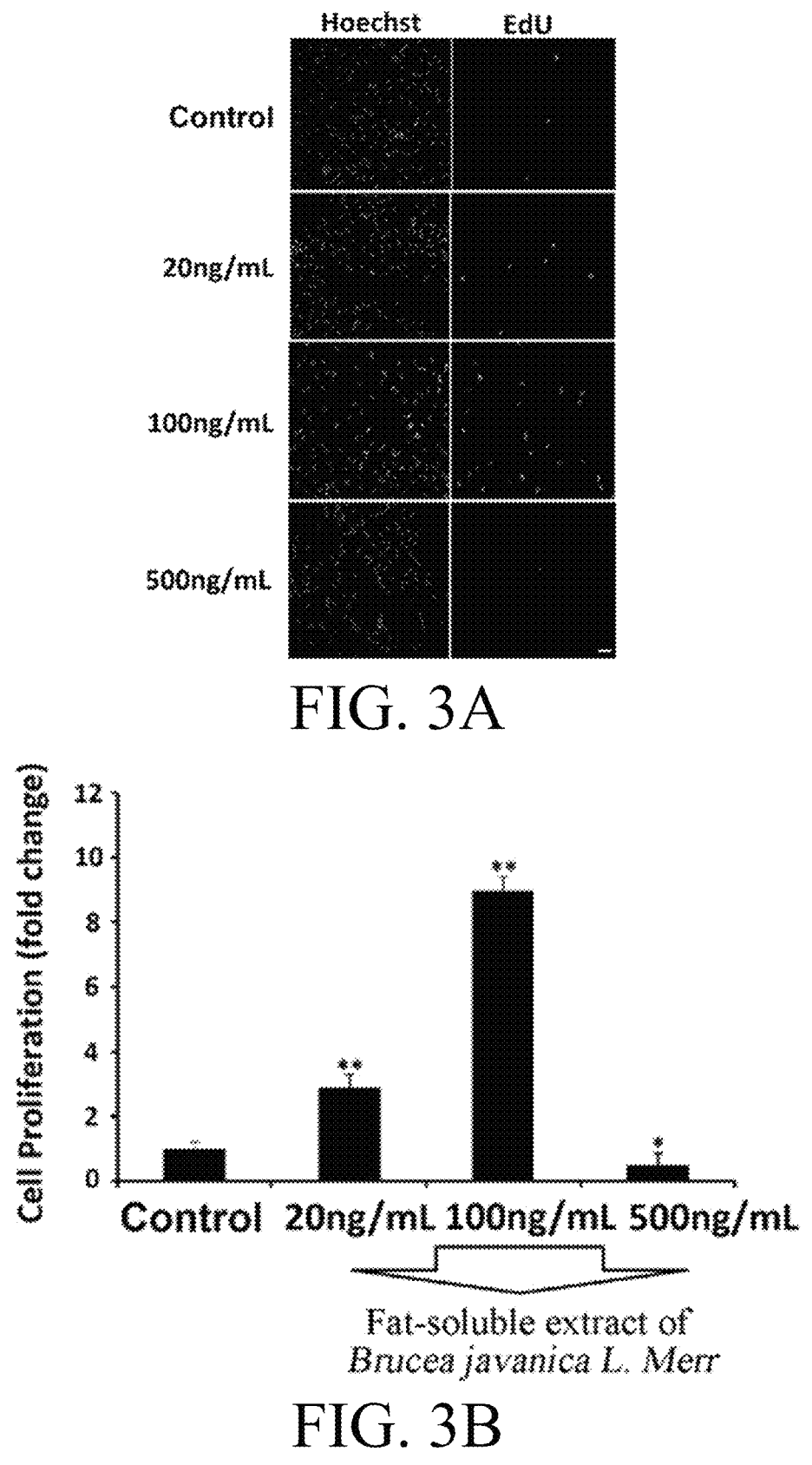

FIGS. 3A and 3B show EdU staining to detect the effect of the fat-soluble extract of *Brucea javanica* L. Merr on the proliferation of Schwann cells. (FIG. 3A shows the EdU staining of Schwann cell proliferation promoted by various dosages of the fat-soluble extract of *Brucea javanica* L. Merr; and FIG. 3B is a histogram showing the statistical result of Schwann cell proliferation promoted by various dosages of the fat-soluble extract of *Brucea javanica* L. Merr. The results show that for the cultured primary Schwann cells treated with different concentrations of the fat-soluble extract of *Brucea javanica* L. Merr, the fat-soluble extract of *Brucea javanica* L. Merr at a concentration of 100 ng/ml can significantly promote the proliferation of Schwann cells compared with the negative control group and the group treated with a low concentration of 20 ng/ml; however, when the concentration is 500 ng/ml, it has a significant inhibitory effect on the proliferation of Schwann cells, suggesting that the fat-soluble extract of *Brucea javanica* L. Merr can significantly promote the proliferation of Schwann cells at an appropriate concentration of 100 ng/ml (Scale bar 20 μm). (**$p<0.01$*$p<0.05$).

Example 6. Promotion of the Fat-Soluble Extract of *Brucea javanica* L. Merr on the Recovery of Nerve Function in Rat Sciatic Nerve Defect Model Animal experiment and groups: SD rats were randomly divided into 4 groups (9 in each group), including a negative control group with saline, and experimental groups with different dosages of the fat-soluble extract of *Brucea javanica* L. Merr, including 5 mg/kg, 15 mg/kg, 30 mg/kg and 45 mg/kg. Model preparation and drug treatment: A compound anaesthetic agent (0.2-0.3 ml/100 g) was intraperitoneally injected for anesthesia, and the surgical area of the left femur was routinely shaved, disinfected, and draped. A median incision was made at the back of the left thigh. The skin and fascia were cut in sequence, the sciatic nerve was fully exposed to form a 10 mm defect, and the sciatic nerve was bridged with a silicone tube. The control, namely, saline, was added to a silicone tube to serve as the negative control group, and 5 mg/kg, 15 mg/kg, 30 mg/kg and 45 mg/kg of the fat-soluble extract of *Brucea javanica* L. Merr were respectively added to the experimental groups. The incision was closed by routine suture. The model preparation and subsequent breeding and observations were all carried out in an SPF-grade barrier system.

Sciatic Nerve Function Index (SFI) is an Intuitive and Reliable Indicator used to evaluate the sciatic nerve regeneration and nerve function recovery. Footprint experiments were performed at 4 W, 8 W and 12 W after surgery. The rats were kept in a passage with a width of about 15 cm, a height of about 15 cm, and a length of about 80 cm. The white rice paper was folded to have the same length and width as the passage, and placed at the bottom of the wooden passage. The two hindfeet of rats were dipped in red ink, and then they were transferred to one end of the passage. The rats walked to the other end of the passage by themselves, leaving 4-5 footprints by each foot on the rice paper. The footprints at the clear normal side and the operation side were selected, and the toe spreads (including normal toe spread, NTS; and experimental toe spread, ETS), print length (including normal print length, NPL; and experimental print length, EPL), and intermediary toe spreads (including normal intermediary toe spread, NIT; and experimental intermediary toe spread, EIT) were measured. An SFI value of 0 indicates normal, and an SFI value of −100 indicates complete nerve disconnection. The SFI value is calculated according to a formula below:

SFI=−38.3×[(EPL−NPL)/NPL]+109.5×[(ETS−NTS)/NTS]+13.3×[(EIT−NIT)NIT]−8.8

Figure 4:
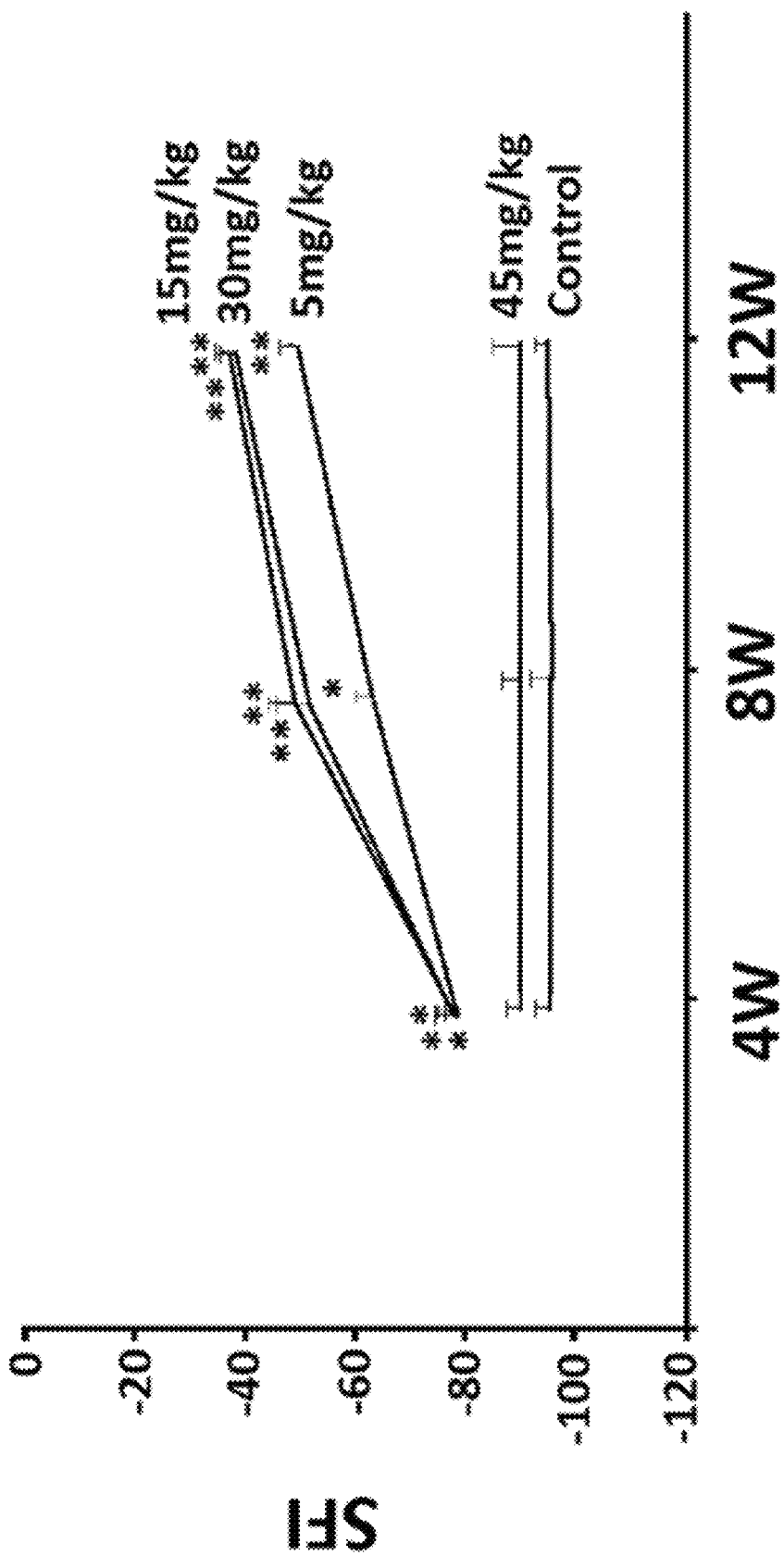
FIG. 4 shows the sciatic nerve function index in a rat sciatic nerve defect model after the fat-soluble extract of Brucea javanica L. Merr is applied.

FIG. 4 shows the sciatic nerve function index in a rat sciatic nerve defect model after different concentrations of the fat-soluble extract of *Brucea javanica* L. Merr are applied. The results show that a promotion on the recovery of nerve function is shown at a low dose of 5 mg/kg, the most significant effect of promoting the recovery of nerve function is achieved at a medium dose of 15 mg/kg, and a dose of 30 mg/kg still falls within the most preferred dose range, which all have significant effect than the negative control group with saline. However, there is no significant difference between the group treated with a high dosage of 45 mg/kg and the negative control group with saline. The most preferred dosage of the fat-soluble extract of *Brucea javanica* L. Merr in vivo to promote peripheral nerve regeneration is 15 mg/kg. (**p<0.01 *p<0.05).

Example 7. Preparation of Various Protein-Modified PLGA-Fat-Soluble Extract of *Brucea javanica* L. Merr Sustained-Release Microspheres Poly(lactic acid)-glycolic acid copolymer (PLGA, molar ratio of lactic acid:ethanol 53:47, molecular weight [MW] 50-75 kDa, Sigma). 100 mg of PLGA was dissolved in 1 mL of dichloromethane to form an oil phase. The PLGA oil phase was emulsified to form 3 mL of 7% (w/v) polyvinyl alcohol (PVA) aqueous solution, which was ultrasonicated for 1 min to prepare an emulsion I. The emulsion I was further added to 50 mL of 1% (w/v) polyvinyl alcohol (PVA) aqueous solution (containing 2% isopropanol) by a two-step emulsification method, and ultrasonicated for 3 min to prepare an emulsion II. The emulsion II was slowly stirred at room temperature overnight, and centrifuged at 13,000 rpm for 5 min at 4° C. to obtain PLGA microspheres.

A suitable amount of collagen, Fibronectin, silk fibroin or laminin was dissolved in sterile pure water to obtain an aqueous solution containing 1 mg/ml collagen, fibronectin, silk fibroin or laminin respectively. At room temperature, 0.4 mL of PLGA microsphere aqueous solution (10 mg/mL) was slowly added with stirring, 5 ml of genipin (0.8 mg/ml) was added as an auxiliary crosslinking agent, and the reaction was continued for 90 min. Then, 10 mL of 10 mg/ml fat-soluble extract of *Brucea javanica* L. Merr was added respectively to 20 mL of 1 mg/ml aqueous solution of the above four protein-modified PLGA microspheres, mixed well and stirred overnight at 4° C., to form light-blue various protein-modified PLGA-fat-soluble extract of *Brucea javanica* L. Merr sustained-release microspheres separately.

The release rate of the fat-soluble extract of *Brucea javanica* L. Merr from various protein-modified PLGA-fat-soluble extract of *Brucea javanica* L. Merr was detected by HPLC. At room temperature, the leachate from each group of microspheres was collected on days 0, 1, 4, 7, 10 and 14, and stored at −20° C. After the samples at all the detection time points were collected, they were detected collectively. Chromatographic conditions: Shimadzu LC-6AD liquid chromatograph. The detection solution was added to 2 mL of deionized water: methanol (4:6, v/v). Chromatographic column X amide column with an inner wall diameter of 150 mm×4.6 mm, particle diameter 5 and pore diameter 100 Å. Mobile phase I: water, mobile phase II: acetonitrile, and mobile phase III: ammonium formate aqueous solution (100 mM, pH3.2). The detection parameters were set as follows: room temperature 22° C., methanol:water=6:4 (v/v) as mobile phase, gradient elution, detection wavelength 266 nm, volume of injection 20 μL, and flow rate 1 mL/min. The result is as shown in FIG. 1.

Figure 5:
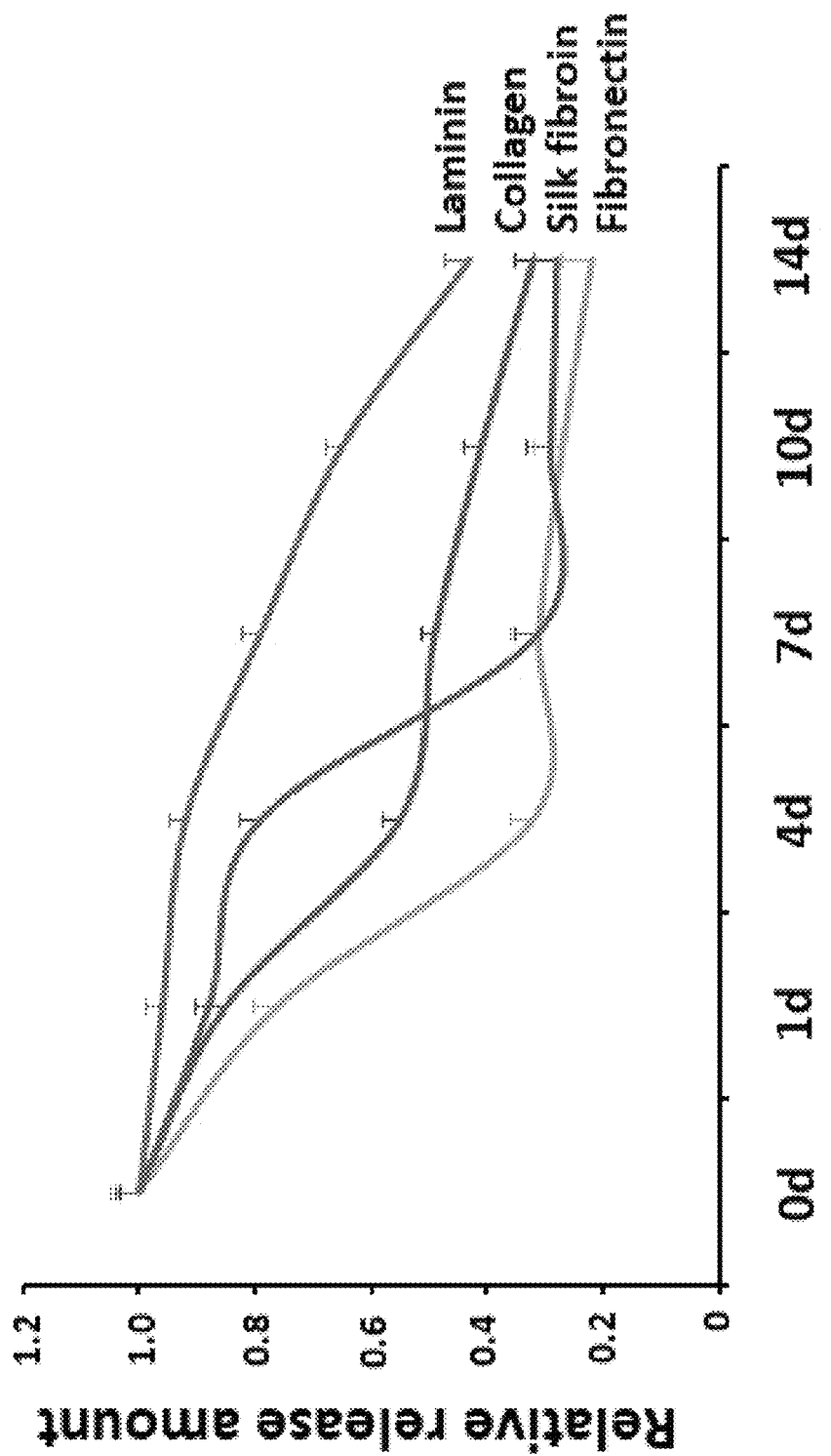
FIG. 5 shows release of the fat-soluble extract of Brucea javanica L. Merr from various protein-modified PLGA sustained-release microspheres detected by HPLC.

The HPLC test results in FIG. 5 show that the release effect of collagen and fibronectin modified PLGA microspheres declines obviously from day 4, and silk fibroin modified PLGA microspheres show waterfall release in days 4-7. The sustained release effect of PLGA microspheres modified by the above three proteins is weak. Laminin-modified PLGA microspheres can release the fat-soluble extract of *Brucea javanica* L. Merr, at a release rate showing a slow and uniform gradient and reaching 79% at 7 days and still 43% at 14 days, with a long slow release period. The results show that the laminin-modified PLGA microspheres has the best effect in releasing the fat-soluble extract of *Brucea javanica* L. Merr, and the sustained release effect is more desirable.

Example 8

Effect of different concentrations of laminin modified PLGA-fat-soluble extract of *Brucea javanica* L. Merr sustained-release microspheres on the axon growth of DRG neurons cultured in vitro SD rats at 15 days of pregnancy were conventionally narcotized by intraperitoneally injecting with 10% chloral hydrate (0.2 mL/100 g). Fetal rats were removed and placed in precooled D-Hank's solution. Dorsal root ganglions (DRGs) were removed under a dissecting microscope, digested with 0.25% trypsin at 37° C. for 15 min, and then terminated with a serum-containing medium. After centrifugation, the cells were adjusted to have a cell density of $5\times10^5$/mL, inoculated in a PDL-coated 24-well plate, and cultured with a DMEM complete medium containing 10% FBS in an incubator at 37° C. and 5% $CO_2$. After the cells were attached, the medium was replaced by 97% Neurobasal+2% B27+1% GluMAX neuron culture medium. The negative control group was a control group without sustained-release microspheres cultured with neuron culture medium. According to the method of Example 7 (prepared with 50 mg/ml fat-soluble extract of *Brucea javanica* L. Merr), DRG neurons in the experimental groups were respectively treated for another 72 hrs with laminin modified PLGA-fat-soluble extract of *Brucea javanica* L. Merr sustained-release microspheres prepared with 0.11 mg/ml, 0.33 mg/ml, 1 mg/ml, 3 mg/ml and 9 mg/ml laminin.

After the DRG neurons were cultured for 72 hours according to the above method, the medium was aspirated, and the cells were washed once with 0.01 M PBS. 500 μL of 4% paraformaldehyde was added, and the cells were fixed at room temperature for 30 min. The fixative was removed, and the cells were washed with 0.01 M PBS for 10 min (×3) at room temperature. The plate was blocked with 0.01 M PBS containing 10% goat serum and 0.3% Triton X-100 at 37° C. for 60 min, and then the blocking buffer was removed. Fluorescence immunocytochemical analysis: The primary antibody (goat anti-NF—H polyclonal antibody, 1:250) was dripped, stood overnight at 4° C., and washed with 0.1 M PBS for 10 min (×3). The secondary antibody (FITC donkey anti-goat IgG, 1:200) was dripped, and the cell nucleus was labeled with Hoechst33342 (5 μg/ml), stood at room temperature for 1 hr in the dark. The cells were then washed with 0.01 M PBS for 10 min (×3). A blank control group without primary antibody was set in the experiment. For the blank control group, the steps were the same as above except that in the step (3), the goat anti-N—H polyclonal antibody was replaced by 0.01 M PBS. Under a laser confocal microscope (FITC excitation wavelength: 488 nm, observation wavelength: 500-535 nm; Hoechst33342 argon-ion Ar excitation wavelength: 353-364 nm, observation wavelength: 460-480 nm), the results of fluorescence immunocytochemical staining were observed. DRG neurites was measured by ImageJ software, statistically calculated by One way ANOVA, and plotted.

Figure 6A:
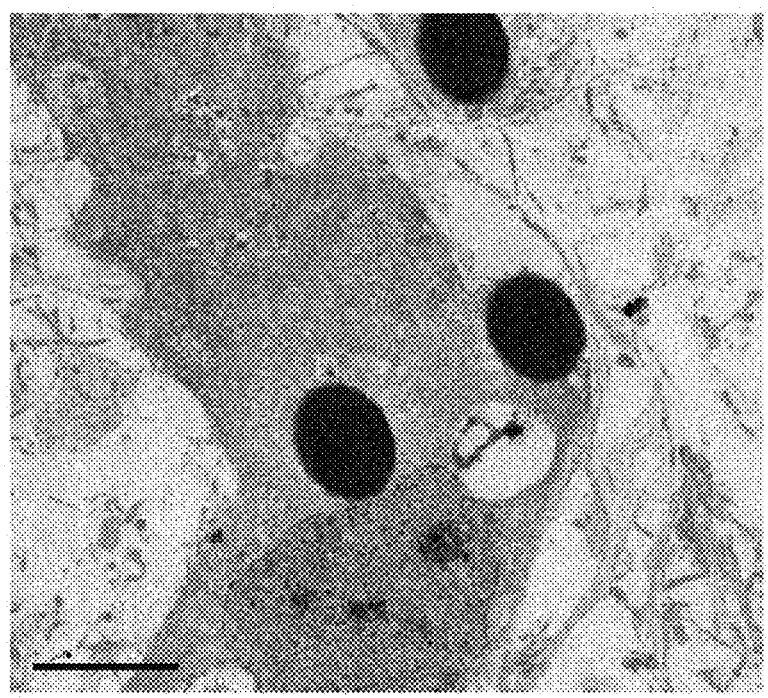
FIGS. 6A-6C show the effect of microspheres and different concentrations of laminin modified sustained-release microspheres on the axon growth of DRG neurons observed under an electron microscope (FIG. 6A is a representative transmission electron microscopy image of laminin-PLGA-fat-soluble extract of Brucea javanica L. Merr sustained-release microspheres.
Figure 6B:
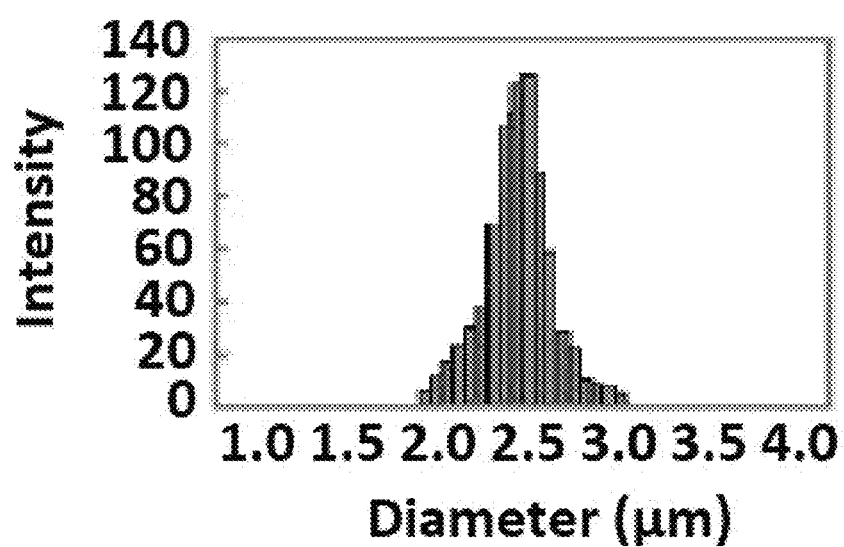
Figure 6C:
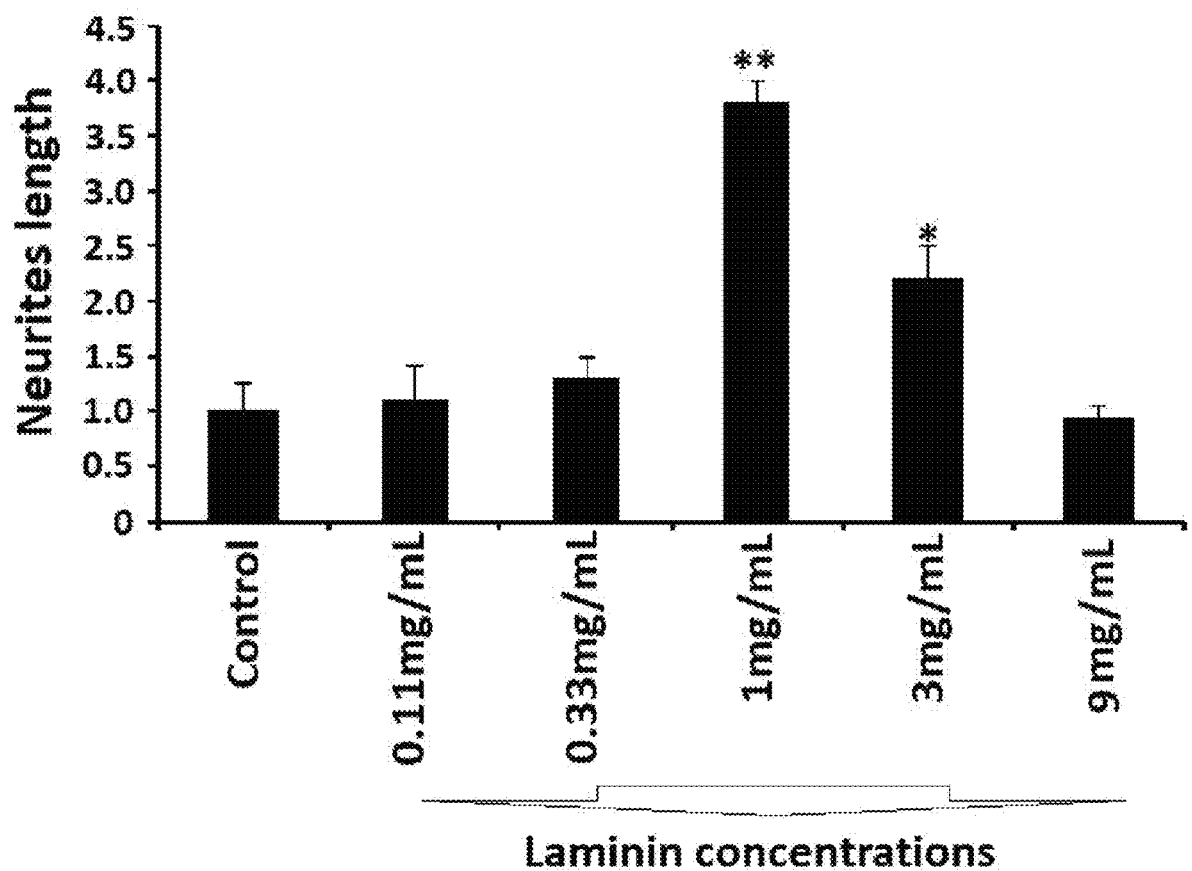

FIGS. 6A-6C show the morphology of microspheres observed under a transmission electron microscope, and the effects of different concentrations of laminin modified PLGA sustained-release microspheres on the growth of DRG neurites. FIG. 6A is a representative transmission electron microscope image of laminin-PLGA-the fat-soluble extract of Brucea javanica L. Merr sustained-release microspheres. The results show that the prepared sustained-release microspheres have smooth surface and uniform particle size (bar=5 μm). FIG. 6B is a histogram of the diameter of the sustained-release microspheres, showing that the diameter of microspheres is mostly concentrated at 2.5 FIG. 6C is a histogram of fluorescence immunocytochemical staining. The results show that the axon length of DRG neurites in the group with sustained-release microspheres prepared with 1 mg/ml laminin reaches 3.8 which is significantly different from that in the control group without slow-release microspheres (**$p<0.01$). In the group with microspheres prepared with 3 mg/ml laminin, the axon length of DRG neurites is 2.2 which is significantly different from that in the control group without slow-release microspheres (*$p<0.05$). They are obviously superior to the axon lengths in the groups with sustained-release microspheres prepared with a higher concentration of 9 mg/ml and lower concentrations of 0.11 mg/ml and 0.33 mg/ml laminin. This indicates that the PLGA sustained-release microspheres prepared with 1 mg/ml laminin have the most preferred effect in release of the fat-soluble extract of Brucea javanica L. Merr.

Example 9. Construction of Tissue-Engineered Nerve Containing the Fat-Soluble Extract of Brucea javanica L. Merr Bombyx mori silk was degummed fully by boiling in 0.05 M $Na_2CO_3$ aqueous solution for 30 min (×2), washed with deionized water, and air dried at room temperature to obtain silk fibroin fibers with a diameter of 10-30 which was sterilized at high temperature under high pressure for later use. Genipin having excellent biocompatibility was used as a crosslinking agent, and the bifunctional groups were respectively linked to the side-chain amino groups of silk fibroin and PLGA. Following the method of Example 7 (prepared with 1 mg/ml laminin), the laminin modified PLGA sustained-release microspheres without the fat-soluble extract of Brucea javanica L. Merr for use in the negative control group, and the laminin modified PLGA sustained-release microspheres prepared with different concentrations of fat-soluble extract of Brucea javanica L. Merr, including 2 mg/mL, 10 mg/mL, 50 mg/mL and 250 mg/mL, were prepared respectively. 10 mL of sustained-release microspheres of each group were immobilized on silk fibroin fibers to obtain silk fibroin fibers loaded with laminin modified PLGA microspheres with different doses of the fat-soluble extract of Brucea javanica L. Merr.

Also, the degummed silk fibroin fibers were dissolved in a ternary solvent system $CaCl_2/H_2O/EtOH$ (molar ratio 1:8:2) at 80° C. for 1 hr. The solution was placed in a cellulose tube (molecular weight cut-off: 12,000-14,000), dialyzed against distilled water, and allowed to stand at room temperature for 3 days. The dialyzed solution was concentrated by rotary evaporation at 40° C. The silk fibroin conduit was molded by a stainless steel casting mold. The mold was composed of a sleeve and a strut in the sleeve, and the distance between the sleeve and the inner strut determined the thickness of the conduit wall. The prepared silk fibroin nerve conduit is 10 mm in length, 2.2 mm in outer diameter and 1.5 mm in inner diameter. The silk fibroin fibers containing laminin modified PLGA-fat-soluble extract of Brucea javanica L. Merr sustained-release microspheres were fit into the silk fibroin nerve conduit. Generally, ten silk fibroin fibers containing the fat-soluble extract of Brucea javanica L. Merr sustained-release microspheres were loaded into each silk fibroin nerve conduit in parallel, to construct the tissue-engineered nerve containing the fat-soluble extract of Brucea javanica L. Merr.

Example 10. Use of Tissue-Engineered Nerve Containing the Fat-Soluble Extract of Brucea javanica L. Merr in Repairing Rat Sciatic Nerve Defect Model Animal experiment and groups: SD rats were randomly divided into 5 groups (6 rats in each group). The negative control group was treated with tissue-engineered nerves constructed with laminin modified PLGA sustained-release microspheres without the fat-soluble extract of Brucea javanica L. Merr, and the experimental groups were respectively treated with tissue-engineered nerves constructed with laminin modified PLGA sustained-release microspheres loaded with different doses of fat-soluble extract of Brucea javanica L. Merr (including 2 mg/mL, 10 mg/mL, 50 mg/mL, and 250 mg/mL fat-soluble extract of Brucea javanica L. Merr) prepared in Example 3. Model preparation and drug treatment: A compound anaesthetic agent (0.3 ml/100 g) was intraperitoneally injected for anesthesia, and the surgical area of the left femur was routinely shaved, disinfected, and draped. A median incision was made at the back of the left thigh. The skin and fascia were cut in sequence, the sciatic nerve was fully exposed to form a 10 mm defect. The tissue engineered nerves in the negative control group and the experimental groups were used to bridge the severed sciatic nerve, and the incision was closed by routine suture. The model preparation and subsequent breeding and observations were all carried out in an SPF-grade barrier system.

Twelve weeks after operation, trichrome staining of the nerve was performed. The following staining reagents were prepared. (1) Harris hematoxylin: 0.5 g of hematoxylin was added to and dissolved in 5 ml of absolute ethanol. 10 g of aluminum potassium sulfate to was added to and dissolved in 100 ml of double distilled water. The two solutions were mixed and heat to boiling. Then, 0.25 g of yellow mercury oxide was added, dissolved, and cooled in ice water. After filtering, 5 ml of glacial acetic acid was added. (2) Trichrome staining solution: 0.3 g of solid green FCF, 0.6 g of Chromotrope 2R and 0.6 g of phosphotungstic acid were sequentially added to and dissolved in 100 ml of double distilled water. Then 2 ml of glacial acetic acid was added to adjust the pH to 3.4. (3) 0.3% glacial acetic acid solution: It was prepared immediately before use. Following appropriately modified experimental methods of Meyer et al., (1) the sections were conventionally deparaffinated into dd$H_2O$; (2) the sections were stained in harris hematoxylin for 5 min; (3) then the sections were washed with double distilled water for 5 min, and the degree of bluing was controlled under a microscope; (4) the sections were stained with the trichrome staining solution for 30 min; (5) then the sections were washed with 0.3% glacial acetic acid twice for 20 sec each and then with running water for 5-10 min, until the sectioned tissue was not decolorized; and (7) the sections were dehydrated to become transparent and then encapsulated with a neutral gum. One-way ANOVA analysis was performed on the data for morphometric analysis of the trichrome staining of the nerve by STATA7 statistical analysis software. If the difference between groups is statistically significant (p<0.05), pairwise comparison was further performed by Turkey's test. The results are expressed as the mean±standard deviation (X±SD).

FIGS. 7A and 7B show trichrome staining of the nerve to observe the myelination of regenerated nerve after repair with a tissue-engineered nerve. FIG. 7A shows a representative graph of the trichrome staining results of each group of nerves, where a is the Control group, and the experimental groups are groups with tissue engineered nerves prepared with 2 mg/mL (b), 10 mg/mL (c), 50 mg/mL (d) and 250 mg/mL (e) fat-soluble extract of *Brucea javanica* L. Merr (bar=5 μm). The statistical results of the trichrome staining results of the nerve in FIG. 7B show that the myelin sheath thickness of regenerated nerve achieved by using the tissue-engineered nerve prepared with 10 mg/mL fat-soluble extract of *Brucea javanica* L. Merr is better than that in the negative control group (**p<0.01). The axon diameter and myelin sheath thickness of regenerated nerve achieved by using the tissue engineered nerve prepared with 50 mg/mL fat-soluble extract of *Brucea javanica* L. Merr are significantly different from those in the negative control group (**p<0.01, *p<0.05).

What is claimed is:

1. A protein-modified polylactic-co-glycolic acid (PLGA) microsphere, comprising PLGA cross-linked with laminin through a cross-linking agent, wherein the microsphere is loaded with one or more active substances selected from *Gastrodia* extract and fat-soluble extract of *Brucea javanica* L. Merr.

2. The microsphere according to claim 1, wherein a weight ratio of laminin to PLGA is 1:1-10.

3. The microsphere according to claim 2, wherein the weight ratio of laminin to PLGA is 1:3.

4. The microsphere according to claim 1, wherein the microsphere is for treating peripheral nerve injury.

5. A method for treating peripheral nerve injury or tissue-engineered nerves, comprising administering an effective amount of the microsphere according to claim 1 to a subject in need thereof.

6. A tissue-engineered nerve loaded with the microsphere according to claim 1, wherein the microsphere is loaded on an inner/outer surface or inside of the tissue-engineered nerve.

7. The tissue-engineered nerve according to claim 6, wherein the microsphere is loaded on the inner/outer surface or inside of the tissue-engineered nerve by one or more method selected from adsorption, coating, mixing, embedding, crosslinking with a crosslinking agent, three-dimensional printing, and electrostatic spinning.

* * * * *